United States Patent [19]
Lay

[11] 4,197,839

[45] Apr. 15, 1980

[54] PASSIVE EXERCISE APPARATUS

[76] Inventor: Kenneth G. Lay, 25 Homer Ave., Cambridge, Mass. 02138

[21] Appl. No.: 867,823

[22] Filed: Jan. 9, 1978

Related U.S. Application Data

[63] Continuation-in-part of Ser. No. 716,125, Aug. 20, 1976, Pat. No. 4,067,326.

[51] Int. Cl.2 .................... A61F 5/00

[52] U.S. Cl. .................... 128/69; 272/144; 272/111

[58] Field of Search .................... 272/144–145, 272/113, 111, 56.5 R; 128/69-70, 71-72, 82-83

[56] References Cited

U.S. PATENT DOCUMENTS

| | | | |
|---|---|---|---|
| 2,929,375 | 3/1960 | Spinks | 272/144 X |
| 3,114,545 | 12/1963 | Horn | 272/111 |
| 3,601,397 | 8/1971 | Carlin et al. | 272/113 X |
| 3,682,475 | 8/1972 | Walker | 272/145 |
| 3,814,416 | 6/1974 | Munger et al. | 272/113 X |
| 3,857,561 | 12/1974 | Cecchettini et al. | 272/144 |
| 3,866,605 | 2/1975 | Stakeman | 128/70 |
| 4,067,326 | 1/1978 | Lay | 128/69 |
| 4,072,309 | 2/1978 | Wilson | 272/144 X |

FOREIGN PATENT DOCUMENTS

| | | | |
|---|---|---|---|
| 966523 | 4/1975 | Canada | 272/144 |

*Primary Examiner*—Robert E. Bagwill
*Attorney, Agent, or Firm*—Jerry Cohen

[57] ABSTRACT

Passive exercise apparatus comprises a chair or rod form of slim supporting struts engaging a limited portion of the back (the middle third) or side arms and legs and affording multiple positions of usage to allow work on several body portions through gravity induced passive exercise of the several portions.

4 Claims, 16 Drawing Figures

PASSIVE EXERCISE APPARATUS

CROSS REFERENCE TO RELATED APPLICATIONS

This application is a continuation-in-part of my copending application Ser. No. 716,125, filed Aug. 20, 1976 and now U.S. Pat. No. 4,067,326, granted Jan 10, 1978. The disclosure of my said copending application is incorporated herein by reference as though set out at length herein.

BACKGROUND OF THE INVENTION

My prior application, above cited, describes apparatus for passive exercise of a chair form or a straight rod form engaging a middle portion of the back and/or other muscles allowing gravitational pull on overhanging muscles to create a situation in which the user applies muscular strains that are beneficial when repeated over a long period. Other parts of the body can be exercised on the same apparatus where the internal strain to maintain balance provides the muscle stimulation without necessarily fighting gravity as such, or as a supplement to the effort to fight gravity working on an overhanging back or other body portion.

It is a particular object of the present invention to provide flexible apparatus of the class described affording many exercise positions.

It is a further object of the invention to provide a sequence of degree of difficulty exercise steps afforded by a single apparatus assemblage.

It is a further object of the invention to provide safe stability for the apparatus itself so that it will not fall over.

SUMMARY OF THE INVENTION

In accordance with the invention there is provided elongated members of generally round form and of lesser width than the back which can be arranged to at least engage the mid back and sides of an adult human user and optionally also the calf muscles. Through relative movement, these members can be adjusted for different users of different dimensions. Other elongated members extending laterally to the first mentioned members can be provided as seat and knee rests for very stable balance for beginners and gradually eliminated in working up to greater degrees of difficulty, in utilization of the apparatus. There are various forms of supporting such apparatus described in several embodiments below, but all having it in common that unexpected tipping over sideways or end on of the apparatus is avoided despite the occasional mistakes of users in setting themselves upon it. In all cases, the angle of the back is adjustable through extremes, including at least the possibility of a 45° (plus or minus 15°) inclination with respect to ground level and a parallel relationship thereto (i.e., 0°).

Other objects, features and advantages will be apparent from the following detailed description of preferred embodiments taken in connection with the accompanying drawing, in which.

DETAILED DESCRIPTION OF PREFERRED EMBODIMENTS

Figure 1:
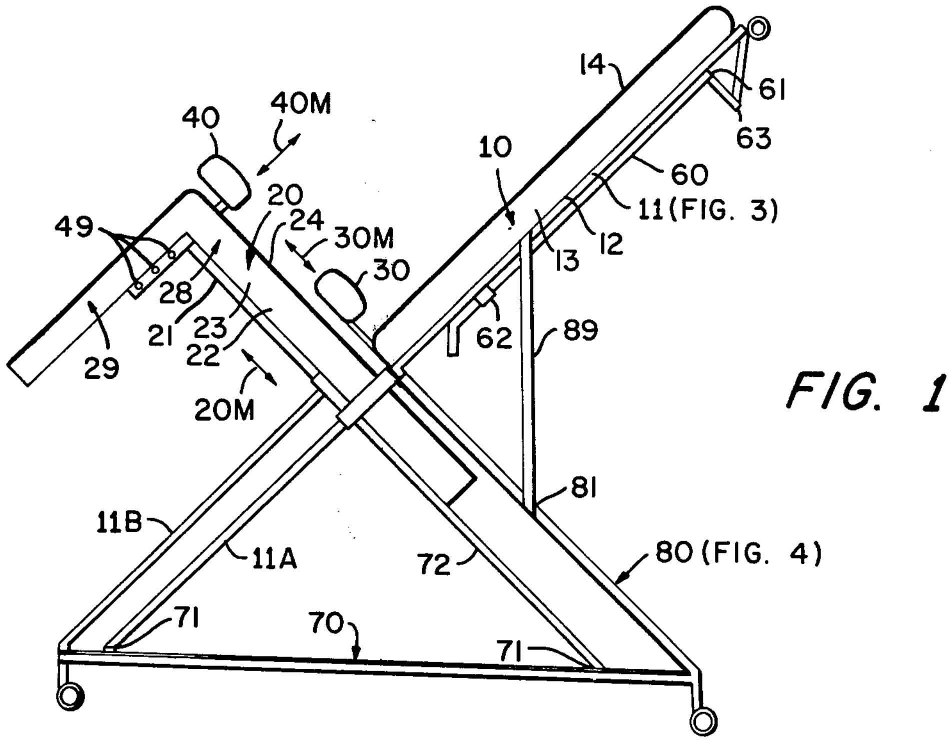
FIG. 1 is a side view of a first preferred embodiment of the apparatus.

There is shown in FIGS. 1–4 a first preferred embodiment comprising an elongated member 10 (FIG. 1) which is made up of (FIGS. 1–1A) a half round of wood 13 bolted to a metal plate 12 which is welded to a square or rectangular piece of metal stock 11 which may be solid or hollow (i.e., tubular). The half round of wood 13 is covered with fabric as indicated at 14. When the apparatus is used as a chair, the member 10 serves as the back. The diameter of the half round of wood can be as little as two inches or as large as 12 inches, but in either case, two to four inches would actually engage the back of a user. The balance of the back muscles would overlap and be drawn down by gravity and this pull would be resisted by bodily muscles in the passive exercise of holding a normal body position and hence providing muscle stimulation. A similar member 20 is provided with sections 28 and 29 a right angles to each other, the section 28 extending generally parallel to or supporting the thighs of a user with the calves and ankles resting along section 29. Each of these sections is constructed in cross sections similarly to element 10 described above. Similar such sections are provided at 30 and 40 as a seat and knee rest. These are arranged transversely to direction of elongation of members 10 and 20 to provide a great width of seat and knee (i.e., backs of the knees) for the novice or inexperienced user. It will be noted that the elements of element 20 including a small crosssection metal stock 21, welded to a plate 22 which is bolted to a half round of wood 23, covered with fabric, are shown.

The elements 20, 30 and 40 are movable as shown by the double headed arrows 20M, 30M and 40M, respectively. There are indicated at 49 pins for securing the knee rest 40 in any of its positions of back or forth movements. A rod 60 is provided housed up against the element 11, and having a pivotal mounting at 51 and frictional holders at 62 and 63 to hold it in two 90° speced extremes of movement. When set out to the extreme where it is locked into holder 63 (like 62, a frictional holder which allows rod 60 to snap in and out) then element 10 can be supported parallel to the ground.

Figure 1A:
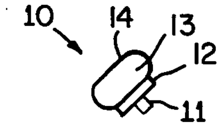
FIGS. 1A and 2–4 are various other projected views of said embodiment or portions thereof.
Figure 2:
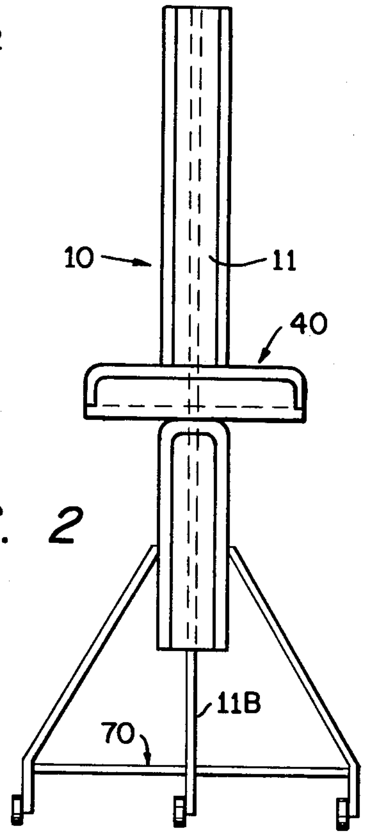
Figure 3:
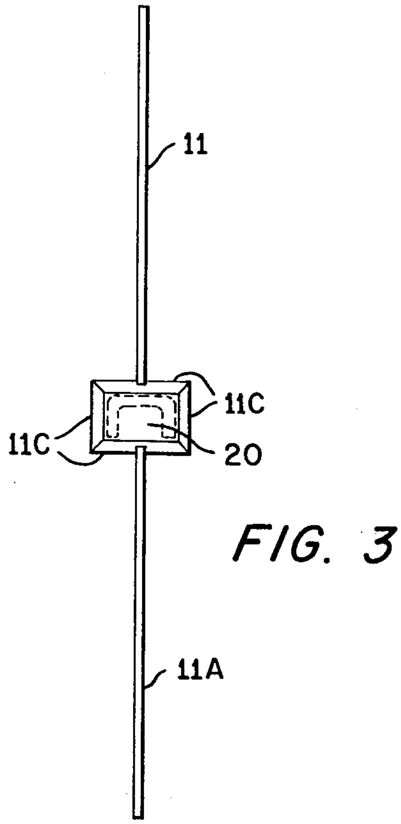
Figure 4:
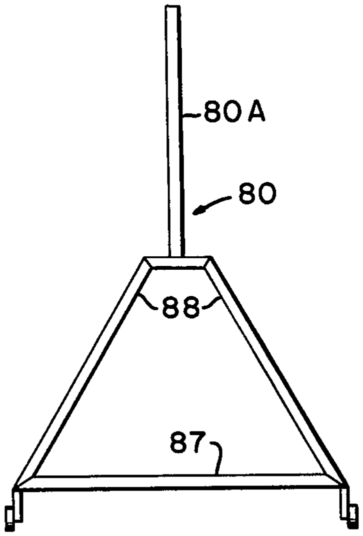

In the support position shown in FIG. 1, general stable support is provided by a triangular truss 70 mounted on three casters C and having two cross members 71 which support a square piece 11A which is an extension of 11 (of FIGS. 1–1A), 11A extending around the element 20 by means of a bridging rectangle made up of four members 11C welded together at wells W and including a support member 80 which passes therethrough (see FIGS. 1, 3 and 4). Support member 80 provides the general support for element 10 and an attaching point for C30 when moved to its various positions. A support member 11B extending up from the foot truss 70 completes the support along with two back legs 72 and provides the basis for sliding support of member 20. In all of the reciprocating or sliding supports described above, there can be a square or a round within a tube or side by side rods or tubes pinned or bolted together in the various positions.

Figure 6:
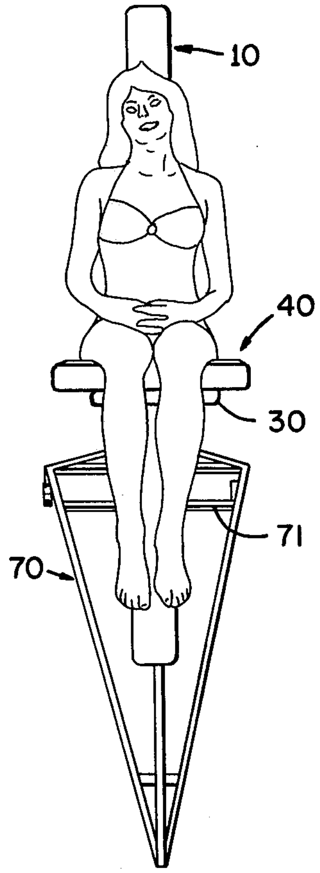
FIG. 6 is a similar photograph, giving a front and top view of the apparatus according to the same embodiment as FIGS. 1–5 and FIGS. 7–12 are similar, on a much smaller scale, photographs of the same apparatus in different positions showing its basic adjustments.
Figure 5:
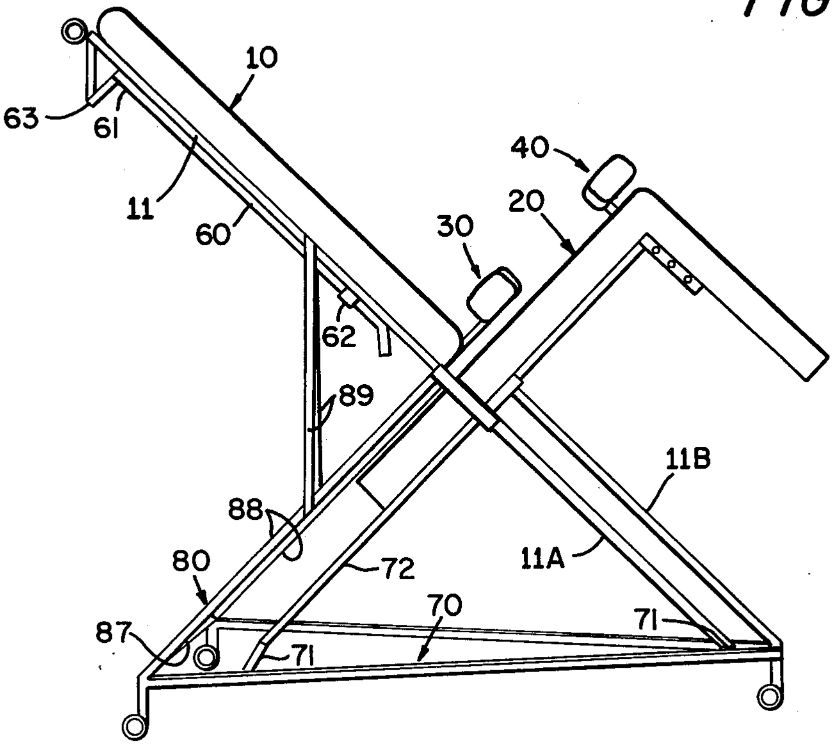
FIG. 5 is a photograph taken at an angle to give an isometric view of the apparatus, essentially from the side.
Figure 7:
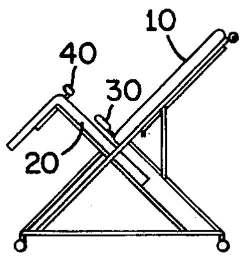
Figure 8:
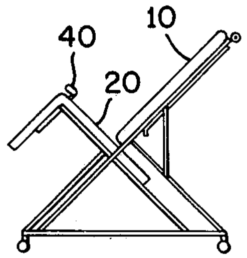
Figure 9:
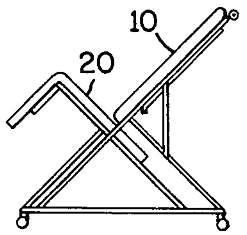
Figure 10:
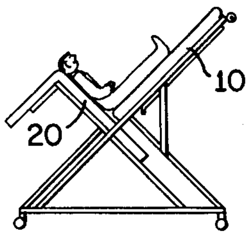
Figure 11:
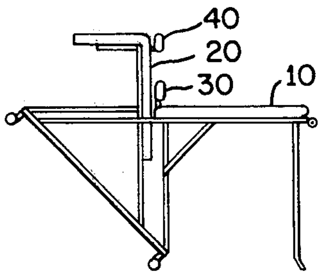
Figure 12:
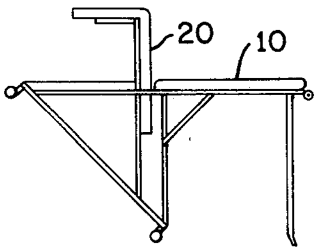

All the foregoing is further illustrated in the photograph isometric in FIG. 5 showing the above described parts and in FIG. 6, a photograpnic view taken from front and slightly above illustrating many of the same parts and in particular illustrating the length of the knee rest 40 and the seat 30 in relation to the width of the user. Knee rest 40 is longer than it has to be to support the knees and this is for the purpose of rotating it and using it (after removing seat 30) as the portion which supports the calves (or can support the back while the feet rest along element 10) by putting 40 to be parallel to element 20 and locking it into the pivoted position.

Without regard to the special position of 40 and assuming only its transverse usage, the various elements are shown in photographs of FIGS. 7-12 in various positions of usage of the chair apparatus ranging from simplest at 7 to most advanced at 12. Initially (FIG. 7) the seat and knee rests are used. Then as the user becomes more advanced and balanced, the seat can be removed, FIG. 8. Then (FIG. 9) the knee rest can be removed. All the while, the apparatus is used as a simple chair with the user's back resting on element 10. Then element 20 can be moved upwardly (FIG.10) and the user can rest his back on element 20 and his legs on element 10.

Then the apparatus is further adjusted so that it can be shifted to the position described above wherein 10 extends parallel to the ground and the seat and knee rest can be provided for assistance and support. Then the more advanced user can dispense with the seat and knee rest and use the apparatus in the position shown in FIG. 12.

Figure 13:
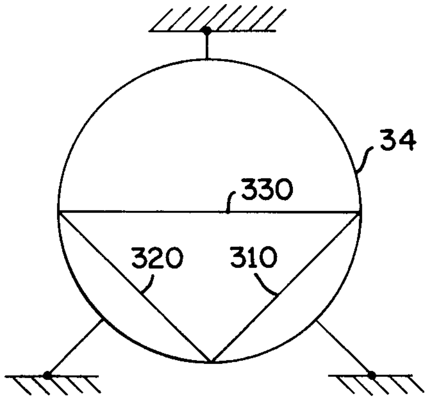
FIGS. 13 and 15 are sketches of a second embodiment of the apparatus in side view form and FIG. 14 is a sketch of a still further embodiment of the apparatus which may be used as such or incorporated into one or both of the previous two mentioned embodiments.

FIG. 13 shows a variation of the apparatus in which three elements arranged as in a triangle, with elements 310, 320 and 330, essentially similar in cross section to the elements 10 and 20 described in FIGS. 1-12, are provided within a ring 340 which can be mounted between the floor F and ceiling CL of a room at three points of support. The user can put his back on 310 and legs stretched out on 320 or vice versa or stretch out on 330. The ring 34 can be rotated to change the angles of the supporting elements to any desired setting. The two dimensional aspect of the FIG. 13 embodiment is convenient for storage, compared to the first embodiment of FIGS. 1-12 wherein stability needs require a three-dimensional spread and greater bulk to avoid tipping over.

Figure 14:
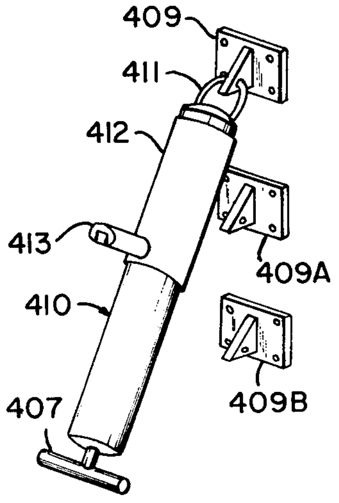

FIG. 14 shows another embodiment of the invention wherein a rod 410 with a tee floor support 407 and a top anchor 411 secured to a wall mounting 409 or alternative wall mountings 409A or 409B for adjustments to different angles is provided for supporting the back with similar exercise benefits to those described in connection with the previous embodiments. The rod 410 is moved or comprises a smooth jacket on a structural core and a sleeve 412 with a fabric shell is slidable thereon. The sleeve 412 may have a stabilizer bar 413 which the user can grip with the inner parts of the thighs for stability. The user leaning his back against sleeve 412 does squats moving his back, constantly in contact with sleeve 412 down and causing sleeve 412 to move with the back and then up. After becoming more advanced, the stabilizer bar 413 which also helps in moving sleeve 412 just by being sat upon. The embodiment of FIG. 14, with or without a stabilizer bar, can be built in to the previously described embodiments as an extra feature thereof, providing active squat exercise as a supplement to the passive exercises of the basic apparatus.

Figure 15:
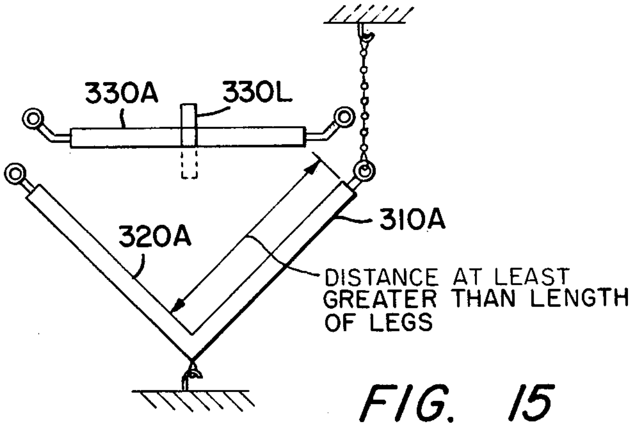

FIG. 15 shows, in exploded form, a variation of the FIG. 13 embodiment wherein the ring is eliminated and separate supports made up of chains and/or hooks H and eyes E or other supports in tension or alternatively compressively loaded struts, not shown) are secured to surrounding building structure to provide lateral stability notwithstanding that the apparatus does not have a three dimensional spread. The struts can be adjusted in relative lengths to adjust angulation of the chain elements.

A lateral support 330 L is removably provided on (and movable along the length of) element 330A for the less advanced user to have support by gripping between the thighs or calf muscles. Elements 330A or alternatively 320A-310A are removable from the assembly. Elements 310A and 320A are at right angles to each other and each is greater than an adult human's leg length.

In all embodiments hereof, the lengthwise spread of support is at least as wide as the length of the seated or reclining user to prevent forward or rearward tipping.

It is evident that those skilled in the art, once given the benefit of the foregoing disclosure, may now make numerous other uses and modifications of, and departures from the specific embodiments described herein without departing from the inventive concepts. Consequently, the invention is to be construed as embracing each and every novel feature and novel combination of features present in, or possessed by, the apparatus and techniques herein disclosed and limited solely by the scope and spirit of the appended claims.

What is claimed is:

1. Passive exercise apparatus comprising, means defining first and second elongated vertically oriented passive exercise elements of at least two inches width at right angles to each other and constructed to seat a person along both elements at once, means for adjusting the angle of such elements relative to horizontal for adjusting degree of difficulty of usage, each such element having a width no more than a narrow mid-section of an adult human back.

2. Passive exercise apparatus in accordance with claim 1 and further comprising, means defining at least one removable auxiliary horizontally oriented support engageable by the user to the apparatus lateral to said first and second elements and attachable to one of said first and second elements to ease usage of the apparatus.

3. Passive exercise apparatus in accordance with claim 1 limited to essentially a single plane and secured to surrounding building structure.

4. Passive exercise apparatus in accordance with claim 1 and further comprising means for extending at least one of the elongated elements parallel to its direction of elongation.

* * * * *